US00PP15512P3

(12) United States Plant Patent
Bradford

(10) Patent No.: US PP15,512 P3
(45) Date of Patent: Feb. 1, 2005

(54) CHERRY TREE NAMED 'GLENROCK'

(50) Latin Name: *Prunus avium*
Varietal Denomination: Glenrock

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 92 days.

(21) Appl. No.: 10/602,669

(22) Filed: Jun. 25, 2003

(65) Prior Publication Data

US 2004/0268452 P1 Dec. 30, 2004

(51) Int. Cl.[7] ..... A01H 5/00
(52) U.S. Cl. ..... Plt./181
(58) Field of Search ..... Plt./181

(56) References Cited

U.S. PATENT DOCUMENTS

PP6,407 P 11/1988 Bradford ..... Plt./181
PP12,859 P2 8/2002 Bradford ..... Plt./181

*Primary Examiner*—Anne Marie Grunberg

(57) ABSTRACT

The present invention relates to a cherry tree, *Prunus avium*, and more particularly to a new and distinct variety broadly characterized by a large size, vigorous, hardy, self-sterile, productive and regular bearing tree. The fruit matures under the ecological conditions described in late May, with first picking on May 24, 2003. The fruit is uniformly large in size, very sweet in flavor, oblate in shape, semi-freestone in type, firm in texture, yellow to red in flesh color, and dark red in skin color.

1 Drawing Sheet

Botanical classification: *Prunus avium.*

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of cherry tree, which has been denominated varietally as 'Glenrock'. During the spring of 1990 I gathered fruit from several 'Tulare' (U.S. Plant Pat. No. 6,407) cherry trees located in my experimental orchard at Bradford Farms near Le Grand, Calif. in Merced County (San Joaquin Valley). The seeds from this fruit were removed, cracked, stratified, germinated, and grown as seedlings on their own root in my greenhouse, and upon reaching dormancy transplanted to a cultivated area of my experimental orchard described above. During the fruit evaluation season of 1995 I selected several cherry trees that exhibited desirable qualities. The present variety was selected as a single tree from the group described above. Subsequent to origination of the present variety of cherry tree, I asexually reproduced it by budding and grafting in the experimental orchard described. above, and such reproduction of plant and fruit characteristics were true to the original plant in all respects. The reproduction of the variety included the use of 'Colt' (unpatented) rootstock upon which the present variety was compatible and true to type.

The present variety is most similar to the 'Glenred' (U.S. Plant Pat. No. 12,859) cherry by producing cherries that are large in size, oblate in shape, firm in texture, dark red in skin color, red in flesh color, and sweet in flavor, but is distinguished therefrom and an improvement thereon by blooming about three days later, by producing cherries that ripen about nine days later, and by being a pollinator for both the 'Glenred' and 'Tulare' (U.S. Plant Pat. No. 6,407) cherries.

SUMMARY OF VARIETY

In summary, the present variety is characterized by a large size, vigorous, hardy, self-sterile, productive and regular bearing tree. The fruit matures under the ecological conditions described in late May, with first picking on May 24, 2003. The fruit is uniformly large in size, very sweet in flavor, oblate in shape, semi-freestone in type, firm in texture, yellow to red in flesh color, and dark red in skin color.

DRAWING

The accompanying photograph displays a characteristic twig bearing leaves, two fruits with the stems attatched, several whole fruits detached from the stems to exhibit the skin color and form, two fruits sectioned along different planes to reveal the flesh and fibers, and two individual leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., at the state of firm ripe on May 25, 2003, on the original tree during the twelfth growing season. All major color code designations are by reference to the Inter-Society Color Council, National Bureau of Standards. Common color names are also used occasionally.

TREE

Size: Large, reaching a height of 16' [4.88 m.] and a spread of 10' [3.5 m.] after twelve growing seasons on its own root.

Vigor: Vigorous, responding typically to irrigation and fertilization. The plant should be grown on a standard commercial rootstock for production purposes.

Growth: Upright.

Form: A natural tendency to generate a central leader system if unpruned, but a vase shape may be obtained by pruning.

Branch angle range: 40 to 90 degrees.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-sterile, must be cross pollinated by another early blooming cherry variety, such as 'Tulare' or 'Sequoia'.

Bearing: Regular bearer with no alternate bearing yet observed.

Trunk:

*Size.*—Medium, with a maximum diameter of 6" [152 mm.] after the twelfth growing season.

*Texture.*—Shaggy.

*Bark color.*—Dark brown [59. d.Br].

*Lenticels.*—Approximate Number Per Square Inch: 8. Color: Moderate brown [58. m.Br]. Typical Size: 3/16" to 5/8" [4.8–15.9 mm.].

Branches:

*Main scaffold diameter.*—2¾" [70 mm.] measured 12" above the crotch.

*Limb diameter.*—1¾" [45 mm.] measured 12" above the first fork.

*Texture.*—Smooth on 1st year wood, increasing roughness with age.

*Color.*—1st Year Wood Topside: Deep purplish red [256. deep pR]. 1st Year Wood Underside: Brilliant yellow green [116. brill.YG]. Older Wood: Brownish gray [64. brGy].

*Lenticels.*—Approximate Number Per Square Inch: 12. Color: Brownish orange [54. brO]. Typical size: ⅛" to ⅜" [3.2–9.5 mm.].

Leaves:

*Size.*—Medium. Average Length: 5" [127 mm.]. Average Width: 2 7/16" [62 mm.].

*Arrangement.*—Alternate.

*Thickness.*—Medium.

*Form.*—Elliptical.

*Apex.*—Acuminate.

*Base.*—Mostly rounded.

*Surface.*—Smooth.

*Color.*—Dorsal Surface: Dark olive green [126. d.OIG]. Vertral Surface: Moderate yellow green [120. mYG].

*Margin.*—Finely serrate.

*Venation.*—Pinnately net veined.

*Vein color.*—Light yellow green [119. l.YG] to Grayish red [19. gy.R].

*Petiole.*—Average Length: 1¼" [31.8 mm.]. Average Thickness: 1/16" [1.6 mm.]. Color: Very dark purplish red [260. v.d.pR] topside with Grayish red [19. gy.R] underside.

*Stipules.*—Number: 2 primary and 4 secondary per leaf. Average Length: 7/16" [11.1 mm]. Color: Grayish red [19. gy.R].

*Glands.*—Number: Usually 2 per leaf. Position: On petiole, typically ¼" [6.4 mm.] below base of blade. Size: Large. Form: Oval to reniform. Color: Dark red [16. d.R].

*Leaf buds.*—Pointed, conic.

Flower buds:

*Hardiness.*—Hardy, with respect to central California winters.

*Diameter.*—Typically 5/16" [7.9 mm.] right before bloom.

*Length.*—Typically ⅝" [15.9 mm.] right before bloom.

*Form.*—Free.

*Surface.*—Nonpubesent.

*Color.*—White [263. white].

Flowers: Perfect, complete, perigynous usually a single pistil, typically twenty or more stamens, five sepals and petal locations alternately positioned.

*Average flower diameter.*—1⅛" [28.6 mm.].

*Number of petals.*—Usally five, but some have a few extra petal fragments.

*Petal shape.*—Circular.

*Petal margin.*—Somewhat wavy with an occasional serration.

*Average petal diameter.*—⅝" [15.9 mm.].

*Average petal length.*—11/16" [17.5 mm.].

*Petal/Apex.*—Rounded with an occasional small notch.

*Petal base.*—Rounded to slightly cuneate.

*Petal color.*—White [263. white].

*Anther color.*—Light yellow [86. l.Y].

*Stigma color.*—Light yellow green [119. l.YG].

*Sepal color.*—Dark purplish red [259. d.pR] over Strong yellow green [117. s.YG].

*Sepal length.*—9/32" [7 mm.].

*Sepal width.*—3/16" [5 mm.].

*Average pistil length.*—⅝" [15.9 mm.].

*Average stamen length.*—½" [12.7 mm.].

*Fragrance.*—Moderate.

*Blooming period.*—Early compared with other varieties.

*Onset of bloom.*—Five percent on Mar. 16, 2003, about three days after 'Glenred' and two days before 'Tulare'.

*Date of full bloom.*—Mar. 25, 2003.

*Duration of bloom.*—Five to ten days, dependent on ambient temperature.

*Number per cluster.*—Usually 2 to 4.

FRUIT

Maturity when described: Firm ripe, May 25, 2003.

Date of first picking: May 24, 2003.

Date of last picking; May 30, 2003.

Size: Uniform, large.

*Average diameter axially.*—⅞" [22.2 mm.].

*Average cheek diameter.*—⅞" [22.2 mm.].

*Average diameter across suture plane.*—1⅛" [28.6 mm.].

*Typical weight.*—0.33 ounces [9.35 grams].

Form: Uniform, symmetrical, compressed axially and around suture.

*Cheek plane form.*—Oblate.

*Suture plane form.*—Oval.

*Axial view form.*—Elliptical.

*Suture.*—An inconspicuous Blackish red [21. blackish R] line located in a shallow groove or trough that extends around the entire fruit.

Ventral surface: Rounded.

Lips: Equal.

Stem cavity: Flaring, circular, suture showing on one side.

*Depth.*—3/16" [4.8 mm.].

*Breadth.*—7/16" [11.1 mm.].

Base: Cordate.

Apex: Rounded to somewhat cordate.

Pistil point: An inconspicuous dot depressed within the suture.
Stem: Medium.
*Average length.*—1½" [38.1 mm.].
*Average width.*—1/16" [1.6 mm.].
*Color.*—Brilliant yellow green [116. brill.YG] with some Grayish red [19. gy.R] tinting from sunlight.
*Attachment.*—Strong.
Skin:
*Thickness.*—Medium.
*Surface.*—Smooth.
*Tenacity.*—Medium.
*Astringency.*—Slightly astringent.
*Tendency to crack.*—Very crack resistant, even in wet season.
*Color.*—Vivid dark red [17. v.d.R] to Deep red [13. deep R].
Flesh:
*Color.*—Pale orange yellow [73. p.OY] with Deep red [13. deep R] streaking with increased maturity.
*Surface of pit cavity.*—Pale orange yellow [73. p.OY] to Dark red [16. d.R] fibers.
*Amygdalin.*—Moderate.
*Juice.*—Abundant, rich.
*Juice color.*—Moderate pink [5. m.Pk].
*Texture.*—Firm, crisp.
*Fibers.*—Abundant, fine.
*Ripens.*—Earliest toward the apex and cheeks.
*Flavor.*—Delicious blend of acid and sugar, 22 brix.
*Aroma.*—Slight.
*Eating quality.*—Best.

STONE

Type: Somewhat freestone.
Form: Oval.
External color: Light grayish yellowish brown [79. l.gy.yBr].
Pit wall color when cracked: Light yellowish brown [76. l.yBr].
Internal cavity color: Light yellowish brown [76. l.yBr].
Average width: 7/16" [11.1 mm.].
Average length: ½" [12.7 mm.].
Average breadth: 5/16" [7.9 mm.].
Hilum: Narrow to oval.
Base: Straight.
Apex: Rounded to acute.
Sides: Equal.
Surface: Smooth.
Ridges: Two thin ridges along the ventral edge.
Average pit wall thickness: 1/16" [1.6 mm.].
Tendency to split: None observed.
Kernel:
*Form.*—Oval.
*Skin color.*—Pale yellow [89. p.Y].
*Pellicle color.*—Grayish yellowish [90. gy.Y].
*Vein color.*—Yellowish gray [93. yGy].
*Taste.*—Bitter.
*Viable.*—Yes.
*Average width.*—¼" [6.4 mm.].
*Average length.*—5/16" [7.9 mm.].
*Amygdalin.*—Abundant.

USE

Market: Fresh market and long distance shipping.
Keeping quality: Good Fruit quality observed to remain in good condition after 14 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of cherry tree, substantially as illustrated and described, that is most similar to the 'Glenred' (U.S. Plant Pat. No. 12,859) cherry by producing cherries that are large in size, oblate in shape, firm in texture, dark red in skin color, red in flesh color, and sweet in flavor, but is distinguished therefrom and an improvement thereon by blooming about three days later, by producing cherries that ripen about nine days later, and by being a pollinator for both the 'Glenred' and 'Tulare' (U.S. Plant Pat. No. 6,407) cherries.

* * * * *

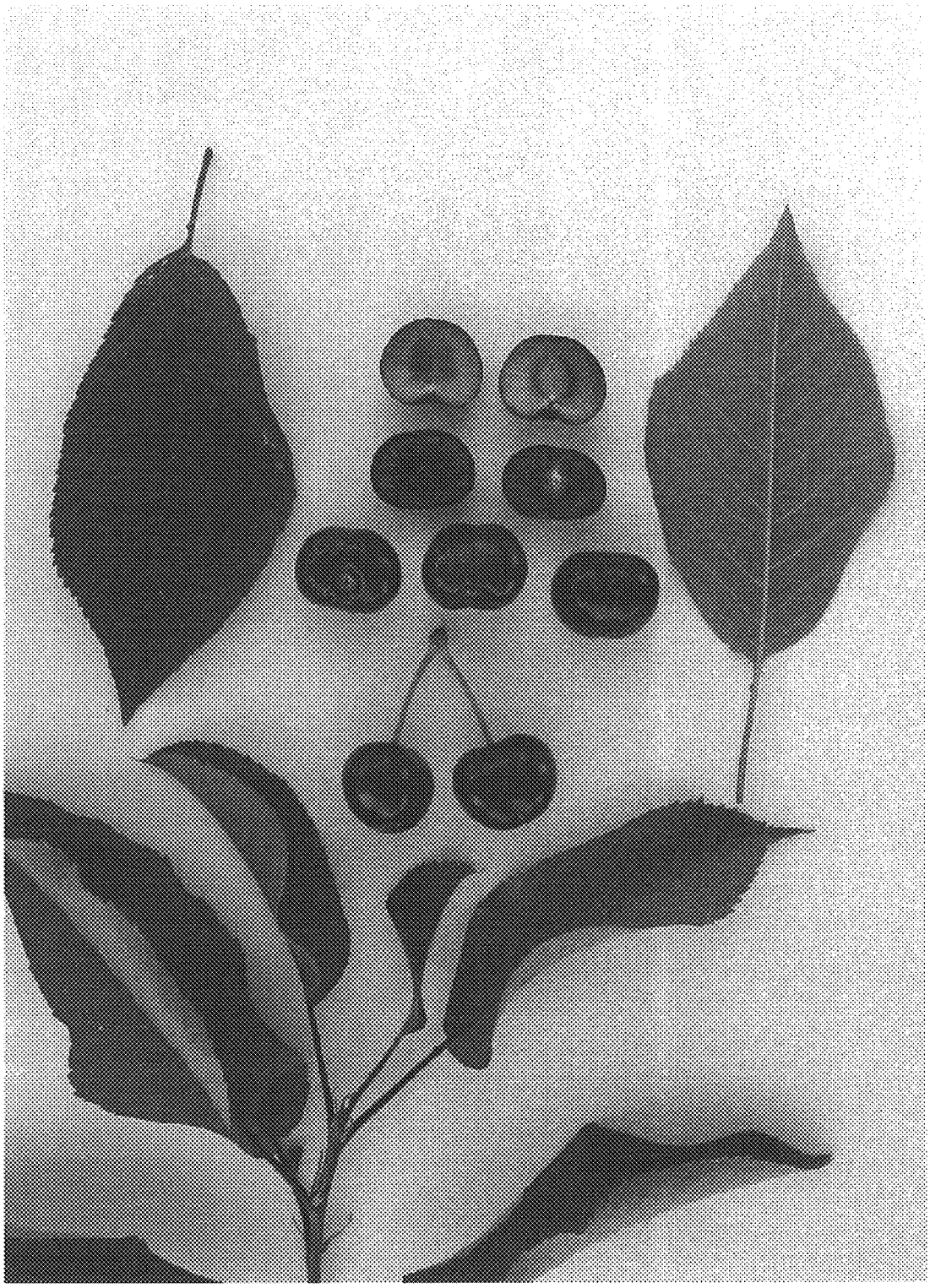

UNITED STATES PATENT AND TRADEMARK OFFICE

CERTIFICATE OF CORRECTION

PATENT NO. : PP 15,512 P3
APPLICATION NO. : 10/602669
DATED : February 1, 2005
INVENTOR(S) : Lowell Glen Bradford It is certified that error appears in the above-identified patent and that said Letters Patent is hereby corrected as shown below:

Column 3: Line 14: Replace "'Sequoia'" with --'Glenred'--

Signed and Sealed this

Seventeenth Day of October, 2006

JON W. DUDAS
*Director of the United States Patent and Trademark Office*